US012642929B2

(12) United States Patent
Saihi et al.

(10) Patent No.: US 12,642,929 B2
(45) Date of Patent: Jun. 2, 2026

(54) PORTABLE RESPIRATORY DEVICE HAVING POWER SUPPLY VIA POWER GRID AND ELECTRICITY STORAGE DEVICE

(71) Applicant: Hamilton Medical AG, Bonaduz (CH)

(72) Inventors: Kaouther Saihi, Chur (CH); Daniel Barandun, Chur (CH); Niko Sinogowitz, Haldenstein (CH); Daniel Zäch, Chur (CH); Gabriele Witton, Chur (CH)

(73) Assignee: Hamilton Medical AG, Bonaduz (CH)

( * ) Notice: Subject to any disclaimer, the term of this patent is extended or adjusted under 35 U.S.C. 154(b) by 956 days.

(21) Appl. No.: 17/786,022

(22) PCT Filed: Dec. 9, 2020

(86) PCT No.: PCT/EP2020/085254
§ 371 (c)(1),
(2) Date: Jun. 16, 2022

(87) PCT Pub. No.: WO2021/122212
PCT Pub. Date: Jun. 24, 2021

(65) Prior Publication Data
US 2023/0020531 A1    Jan. 19, 2023

(30) Foreign Application Priority Data

Dec. 17, 2019    (DE) .................... 10 2019 134 830.7

(51) Int. Cl.
*A61M 16/06*        (2006.01)
*A61M 16/00*        (2006.01)

(52) U.S. Cl.
CPC .......... *A61M 16/06* (2013.01); *A61M 16/022* (2017.08); *A61M 2205/8206* (2013.01)

(58) Field of Classification Search
CPC .......... A61M 16/16; A61M 2205/8206; A61M 2205/8212; A61M 2205/8256; A61M 2205/8262
See application file for complete search history.

(56) References Cited

U.S. PATENT DOCUMENTS

| | | | |
|---|---|---|---|
| 7,225,809 B1 | 6/2007 | Bowen et al. | |
| 8,020,557 B2 | 9/2011 | Bordewick et al. | |

(Continued)

FOREIGN PATENT DOCUMENTS

| | | |
|---|---|---|
| CN | 107103180 A | 8/2017 |
| DE | 202011106203 U1 | 12/2011 |
| EP | 1568391 A1 | 8/2005 |

OTHER PUBLICATIONS

International Preliminary Report on Patentability for corresponding PCT/EP2020/085254 mailed May 17, 2022, 7 pgs.

(Continued)

*Primary Examiner* — Joseph D. Boecker
*Assistant Examiner* — Thomas W Greig
(74) *Attorney, Agent, or Firm* — Rankin, Hill & Clark LLP

(57)        ABSTRACT

A portable respiratory device for supplying respiratory gas to a living being, including: a housing; a respiratory gas conveying apparatus which is designed to convey inspiratory respiratory gas to a respiratory gas housing outlet of the housing; an input/output apparatus for the input of control commands and for the output of information; a control apparatus which is connected to the input/output apparatus and to the respiratory gas conveying apparatus for transferring signals; a first, grid-based power supply which is designed to be connected to a grid voltage source that is external in respect of the respirator device in order to transfer electricity and which is designed and arranged in order to supply electricity to the control apparatus, the (Continued)

input/output apparatus and the respiratory gas conveying apparatus; wherein the respiratory gas conveying apparatus, the input/output apparatus, the control apparatus and the first power supply are received in the housing; the respiratory device has a second, storage-based power supply which has an electricity storage device for storing electrical energy and which is designed at least to supply the respiratory gas conveying apparatus with electricity.

11 Claims, 4 Drawing Sheets

(56)                    References Cited

U.S. PATENT DOCUMENTS

| | | | |
|---|---|---|---|
| 10,195,378 B2 | 2/2019 | Truschel et al. | |
| 2008/0099017 A1* | 5/2008 | Bordewick | A61M 16/0057 |
| | | | 128/204.21 |
| 2011/0162647 A1* | 7/2011 | Huby | A61M 16/16 |
| | | | 128/203.14 |
| 2017/0209662 A1 | 7/2017 | Ahmad et al. | |
| 2018/0185606 A1* | 7/2018 | Van Schalkwyk | A61M 16/024 |
| 2020/0238032 A1 | 7/2020 | Panarello | |
| 2020/0297960 A1 | 9/2020 | O'Donnell et al. | |
| 2020/0306489 A1* | 10/2020 | Wright | A61M 16/16 |

OTHER PUBLICATIONS

German Search Report for corresponding DE 10 2019 134 830.7 mailed Aug. 31, 2020, 8 pgs.

International Search Report for corresponding PCT/EP2020/085254 mailed Apr. 8, 2021 14 pgs.

Espacenet Bibliographic data:DE 202011106203 (U1), Published Dec. 5, 2011, 1 pg.

Espacenet Bibliographic data:EP 1568391 (A1), Published Aug. 31, 2005, 1 pg.

Japanese Office Action for corresponding JP 2022-537156 mailed Apr. 2, 2024, 4 pgs.

Chinese Office Action for corresponding CN 202080087846.7 mailed Apr. 30, 2025, 6 pgs.

Espacenet Bibliographic data: CN107103180 (A), Published Aug. 29, 2017, 1 pg.

* cited by examiner

PORTABLE RESPIRATORY DEVICE HAVING POWER SUPPLY VIA POWER GRID AND ELECTRICITY STORAGE DEVICE

This application claims priority in PCT application PCT/EP2020/085254 filed on Dec. 9, 2020, which claims priority in German Patent Application DE 10 2019 134 830.7 filed on Dec. 17, 2019, which are incorporated by reference herein.

Portable respiratory device for supplying respiratory gas to a living organism, comprising:

A housing,

A respiratory gas conveying device which is configured to convey inspiratory respiratory gas to a respiratory gas housing outlet of the housing, An input/output device for the input of control commands and for the output of information, A control device which is connected for signal transmission with the input/output device and with the respiratory gas conveying device, A first, power grid-based power supply which is configured for current-transmitting connection with a power grid voltage source external to the respiratory device and which is configured and arranged for supplying the control device, the input/output device, and the respiratory gas conveying device with current, Where the respiratory gas conveying device, the input/output device, the control device, and the first power supply are accommodated in the housing.

BACKGROUND OF THE INVENTION

Such portable respiratory devices are known first and foremost from high-flow ventilation, according to which a patient is supplied with an essentially constantly high respiratory gas flow regardless of his or her respiratory rhythm. The respiratory gas flow comprises up to 100 liters per minute. The respiratory gas flow is normally provided via nasal cannulas in the region of the nostrils or administered via a nasal-oral mask or via a tracheal cannula, which covers the patient's nose and mouth. During inhalation, the patient thus unavoidably breathes in at least part of the supplied respiratory gas flow. Exhalation takes place against the respiratory gas flow which usually is also supplied during exhalation.

Such respiratory devices usually exhibit a respiratory gas reservoir, for example in the form of a respiratory gas cylinder, in which respiratory gas is accommodated under positive pressure relative to the atmosphere. The respiratory gas conveying device then comprises the respiratory gas cylinder and a pressure-reducing valve, which reduces the respiratory gas stored in the respiratory gas cylinder under high pressure to a respiratory gas pressure tolerable for the patient.

Other portable respiratory devices exhibit a fan as a respiratory gas conveying device, where during its operation the fan is supplied with current by a power grid voltage source.

A drawback in the known solutions is, in the first case, the operating lifetime which given good mobility, is limited by the bottle's content, and in the second case the mobility which given the longest possible operating lifetime, is restricted by the power supply per power grid voltage source.

SUMMARY OF THE INVENTION

It is, therefore, the task of the present invention to provide a portable respiratory device of the type mentioned at the beginning, which offers both a long uninterrupted period of operation and also the most unrestricted mobility possible.

The present invention solves this task in a portable respiratory device as described at the beginning of this application by having the respiratory device exhibit a second, storage-based power supply which exhibits an electricity storage device for storing electrical energy and which is configured at least for supplying the respiratory gas conveying device with current.

Thanks to the second, storage-based power supply, the portable respiratory device is not exclusively dependent on connection to a power grid voltage source, which considerably increases the mobility compared with a portable respiratory device having solely a power grid connection as an energy supply. Consequently it is possible to unlock a nearly unlimited respiratory gas reservoir by means of a fan as a respiratory gas conveying device, thus supplying the patient permanently with respiratory gas. Due to the provided second power supply, which exhibits its own storage of electrical energy, referred to hereunder as "electricity storage device", the range of movement of the patient can temporarily be considerably increased compared with an exclusive power grid supply. Operational phases during which the respiratory gas conveying device is supplied by a power grid voltage source, i.e. for instance a public power grid, and operational phases during which the respiratory gas conveying device is supplied by the electricity storage device of the second power supply, can alternate. The longest possible operating lifetime with at the same time possible mobility is achieved hereby. Thus the ventilated patient can move independently of the power grid, for example within a hospital between different treatment and/or diagnostic wards.

Preferably, therefore, the respiratory gas conveying device comprises a fan which aspirates air from the environment of the respiratory device and conveys it to the respiratory gas housing outlet. During operation, there is usually connected to the respiratory gas housing outlet a respiratory gas conveying line, preferably a flexible respiratory gas hose, in order to conduct respiratory gas from the housing to the patient. The respiratory device is preferably a high-flow respiratory device as mentioned at the beginning.

The respiratory device can exhibit, in addition to the fan, a connecting formation, for example a connecting nozzle or a quick coupling, for connecting a further respiratory gas reservoir different from the ambient air. Thus for example, to the ambient air aspirated by the fan there can be added pure oxygen or another desired gas, a gas mixture, or an aerosol-containing gas. The ambient air aspirated by the fan is therefore preferably conducted via a mixing chamber or a mixing line section, into which there also opens a further line coming from the connecting formation before it reaches the respiratory gas housing outlet.

The storage capacity of the electricity storage device of the second power supply is preferably so dimensioned, that respiratory operation solely through the second power supply can be maintained at least for one hour, preferably for several hours.

To secure the supply of the patient with respiratory gas, in principle it suffices if the second power supply exclusively supplies the respiratory gas conveying device with electrical energy. Preferably, however, beyond the mere supplying of the patient with respiratory gas, the second power supply also serves for the most comprehensive controllability and adjustability possible of the respiratory gas supply of the patient. Therefore it is preferably provided that the second power supply is also configured for supplying the control device and the input/output device with current. Especially preferably, the second power supply serves to supply the same functional devices within the respiratory device as the first power supply, such that according to this especially preferable configuration the second power supply can replace the first power supply to the full extent.

In this case too, preferably the electricity storage device is so dimensioned that the operation of the respiratory device only through the second power supply can be maintained at least for one hour, preferably for several hours.

For the conditioning of the respiratory gas with regard to its humidity content, according to a preferable further development of the present invention the respiratory device can exhibit a humidification device which is configured to humidify the inspiratory respiratory gas. In this process, likewise preferably, the humidification device can be supplied with current both by the first and by the second power supply. This means that the humidification device can be supplied with current either by the first or by the second power supply. For example, the humidification device can exhibit a hot plate or another evaporation device which when operated electrically, vaporizes water or an aqueous solution and thus feeds it to the inspiratory respiratory gas.

A respiratory gas line which leads from the respiratory device to the patient is preferably heatable in order to prevent condensation in the respiratory gas line. This heat output of a heating device of the respiratory gas line can also be electively supplied from the first or from the second power supply. Since electric heating is very energy-intensive, when power is supplied to the respiratory device by the second power supply, preferably the heating device of the respiratory gas line can be switched off in an isolated manner in order to save electrical energy and thus to extend the operating lifetime of the second power supply.

The electricity storage device of the second power supply is preferably rechargeable. To this end, the second power supply can be connected in an electrically conducting manner with a charger, which itself in turn can be connected with a charging electricity storage device or a power grid voltage source. With the objective of keeping the number of devices required for operating the respiratory device or for producing an operational state of it as low as possible, preferably the electricity storage device of the second power supply is chargeable by the first power supply. This is readily possible, since the first power supply is connectable with the power grid voltage source such that from the power grid voltage source sufficient electrical energy is available for charging the electricity storage device of the second power supply. In order to prevent uncontrolled charging of the electricity storage device of the second power supply and thereby possibly over-charging of same, preferably the control device is configured to control a charging process of the electricity storage device by the first power supply. To this end, the control device can continuously or with interruptions interrogate the charging state of the electricity storage device and depending on the interrogation result terminate the charging process.

In order to make sure that in the event of failure of the power grid voltage source, for instance during a blackout of the public power supply or after local switching off of the power grid supply through activation of an electrical cutout, at least the respiratory gas conveying device continues to convey respiratory gas to the patient without risking the latter, preferably the entire respiratory device continues to operate, preferably it is provided that the second power supply is configured as an interruption-free power supply for the event of an ending of a power supply of the respiratory device by the first power supply. An interruption of up to 50 ms of the power supply when switching over from the first to the second power supply is to be regarded customarily in this field as "interruption-free". In the event of a supply termination of the first power supply, because of the medical application preferably the second power supply continues interruption-free in the literal sense the power supply at least of the respiratory gas conveying device, preferably also of other functional devices, such that the supply of power by the second power supply follows seamlessly a supply of power by the first power supply.

In principle, the second power supply can be accommodated in the housing of the respiratory device. Since usually electricity storage devices, as required by the second power supply, exhibit substantial weight due to their above-average density, in order to limit the weight of the portable respiratory device and thereby improve the mobility of the respiratory device, preferably the idea is for the second power supply to exhibit a power supply housing separate from the housing of the respiratory device. Hence the second power supply can, when not needed, be separated from the housing of the respiratory device. This is conceivable, for example, in operational phases in which the respiratory device is supplied with electrical energy solely by the first power supply. Therefore according to a preferable embodiment, the power supply housing of the second power supply is physically couplable in a detachable manner with the housing of the respiratory device for common movement. Thus, when the second power supply is physically coupled with the housing of the respiratory device, it is also transportable together with the latter, such that only one item, comprising the housing and the power supply housing, has to be moved. Thus the person moving the respiratory device always still has one hand free.

The above-average high weight per unit volume of the electricity storage device of the second power supply and thus of the second power supply overall was already mentioned above. In order to make sure that the respiratory device being discussed here exhibits the highest possible stability, when the respiratory device is set up operationally the second power supply is preferably arranged in the lowest 20% of the total vertical extension of the respiratory device having the second power supply. In view of the aforementioned preferable physical coupleability, which includes separability, of the housing and the power supply housing, preferably the second power supply is the lowest functional device in the respiratory device comprising the second power supply, in order to produce not only a low but the lowest possible center of gravity of the respiratory device. The aspect of the lowest possible center of gravity of the respiratory device applies both to the case that the second power supply is coupleable with the housing of the respiratory device and is separable from the latter, and to the case that the second power supply is accommodated in the housing of the respiratory device.

Since the aforementioned humidification device can exhibit a liquid reservoir and thereby likewise an above-average high weight per unit volume, preferably the humidification device, but at least its liquid reservoir, and the second power supply are arranged in immediate proximity. Preferably the humidification device, but at least its liquid reservoir, and the second power supply are arranged one above the other when looking at the operationally ready respiratory device, where preferably the second power supply is arranged under the humidification device.

In order to prevent unexpected trip hazards at the set down respiratory device, preferably the power supply housing—when looking at an operational positioning of the respiratory device—is completely accommodated inside a footprint of the housing of the respiratory device projected in the gravitational direction. Thus the power supply housing does not project sideways beyond the housing of the respiratory device. For reasons of the highest possible stability, preferably the power supply housing, when it forms the lowest functional unit of the respiratory device, also does not retreat behind the footprint of the housing of the respiratory device projected in the gravitational direction. Preferably, the housing and the power supply housing with the exception of an unavoidable joint line between them form a flush outer wall of the overall device consisting of housing and power supply housing.

Since in order to achieve the lowest possible center of gravity, during operational positioning of the respiratory device preferably the second power supply is the lowest functional device of the respiratory device, which for the aforementioned reasons likewise is preferably arranged under a liquid reservoir of a humidification device, it can happen that fluid—be it as leakage from the liquid reservoir or be it as water condensate—running down the housing under the force of gravity, reaches the power supply housing.

In order to prevent damage caused by humidity to the second power supply, the power supply housing is preferably configured to be sealed against humidity.

In order to prevent humidity damage to the surrounding where the respiratory device is positioned, in particular to the positioning surface on which the respiratory device stands during operation, there are preferably configured at the power supply housing drainage surfaces which in a targeted manner drain liquid impinging on them to at least one defined drainage location, where the drained liquid can be anticipated and collected.

The drainage surfaces preferably comprise at least two differently inclined surface sections, which—in the operational orientation of the respiratory device with coupled second power supply—follow one another in the gravitational direction. Preferably a first surface section, due to its first inclination, conducts liquid from the outer wall of the respiratory device inwards into a gap space between the housing and the power supply housing to a second surface section which follows the first surface section in the direction of the first inclination, which due to its second inclination drains the liquid transferred to its from the first surface section to the drainage location. The drainage location is preferably situated at an outer surface of the respiratory device, preferably at the joint line between the housing and the power supply housing. In order to prevent faults in the operation and the activation of the respiratory device through the drained liquid, the drainage location is preferably not at the front side of the respiratory device, but rather preferably at its rear side. There the drained liquid can be collected by an absorbent cloth provided at the release location or just such a sponge.

Since the liquid drainage takes place at a surface of the power supply housing, the first and the second surface section are preferably configured as sections of a surface of the power supply housing, which in the state of being coupled to the housing borders a separating gap between the housing and the power supply housing on the side of the power supply housing.

For the largest possible liquid drainage area, preferably the first surface section proceeds at least section-wise around the housing, because of the gravitationally driven drainage preferably around its vertical axis. Preferably the first surface section extends on the front side and on the two lateral surfaces of the power supply housing adjoining it on different sides. The first surface section can be inclined in the direction towards a body center of the power supply housing, in order to be able to conduct liquid from the outer surface of the respiratory device inwards into the separating gap volume between the housing and the power supply housing. The first surface section can be curved about an axis of curvature, in order to be able to achieve the greatest possible length along the outer wall of the power supply housing. The axis of curvature is therefore preferably different from the inclination axis or the inclination axes of the first surface section.

The second surface section preferably adjoins the first surface section directly. In the simplest case it can be a plane inclined surface, at the geodetically lowest point of which the drainage location is situated.

In order to require the smallest possible base area, the housing is preferably a tower housing whose largest dimension during operational positioning is the vertical dimension. Preferably the housing is at least one and a half times as tall as it is wide and likewise at least one and a half times as tall as it is deep. "Width" and "depth" are here dimensional directions which are orthogonal both to one another and to the vertical direction of the housing.

For easier operating, the housing can exhibit the input/output device at its upper region. Especially good accessibility of operating units of the input/output device can be obtained by having the input/output device exhibit an input/output surface which is inclined and/or curved both in respect of the vertical direction and in respect of the depth direction about a pitch axis proceeding in the width direction, at which operating units, such as for instance buttons, switches, display areas, and the like are arranged or configured.

In order to achieve the longest possible operating lifetime with energy only from the second, storage-device-based power supply, the control device is configured to control and/or to regulate the operation of the respiratory device, in particular of a heating device, preferably of all heating devices in and at the respiratory device, more strongly preferably of the aforementioned hot plate, in accordance with a detection signal of a temperature sensor connected with the control device for signal transmission in such a way that the temperature signal transmitted by the temperature sensor to the control device represents a temperature which does not exceed a predetermined temperature limit. The predetermined temperature limit can lie in the range from 30° C. to 40° C. and preferably lies in the range from 33° C. to 38° C., if it represents a temperature of an inspiratory respiratory gas in the region of the proximal end region of a respiratory gas hose connected to the respiratory device. Preferably the temperature limit is 35° C.

The respiratory device preferably comprises at least one temperature sensor, which detects a temperature of an inspiratory respiratory gas in the region of the proximal end region of a respiratory gas hose connected to the respiratory device and transmits it to the control device. Preferably there is at least one temperature sensor arranged at the respiratory gas hose, namely preferably within a range not exceeding 50 cm, preferably not exceeding 30 cm, before administration of inspiratory respiratory gas to the patient.

In order to maintain respiratory operation over the longest possible time, the control device can be further configured to supply, depending on the charging state of the electricity storage device, only predetermined selected components of the respiratory device with current.

Electrically operated heating devices are especially intensive current consumers. Therefore the control device can be configured to shut down one or several heating devices, depending on the charging state of the electricity storage device. The shutting down can, for example, take place by interrupting the power supply or by switching off. This shutting down can take place in a staggered manner for different components depending on different limit charging states, where different components are assigned quantitatively different limit charging states, dropping below which leads to shutting down of the respective components. Thus when the charging state of the electricity storage device drops below a first limit charging state, the control device can shut down the evaporation device, in particular its hot plate. The pressure-modifying device and other components can continue to be operated. When the charging state drops below a second limit charging state which is quantitatively lower than the first limit charging state, it can be provided to shut down a heating device of the respiratory gas line. Once again, the pressure-modifying device and further components can continue to be operated.

Finally, when there is a drop below a third limit charging state which is quantitatively lower than the second limit charging state, it can be provided that the control device shuts down the respiratory operation. The third limit charging state can be the quantitatively lowest charging state which effects in a targeted manner a shutdown by the control device of one or several components. There can, however, be a further quantitatively lower limit charging state, until the reaching of which data storage devices, in particular volatile data storage devices, are supplied with current in order to be able to output data about the operation or secure them in non-volatile storage media of the respiratory device.

These and other objects, aspects, features and advantages of the invention will become apparent to those skilled in the art upon a reading of the Detailed Description of the invention set forth below taken together with the drawings which will be described in the next section.

BRIEF DESCRIPTION OF THE DRAWINGS

The invention may take physical form in certain parts and arrangement of parts, a preferred embodiment of which will be described in detail and illustrated in the accompanying drawings which forms a part hereof and wherein.

DESCRIPTION OF PREFERRED EMBODIMENTS

Figure 1:
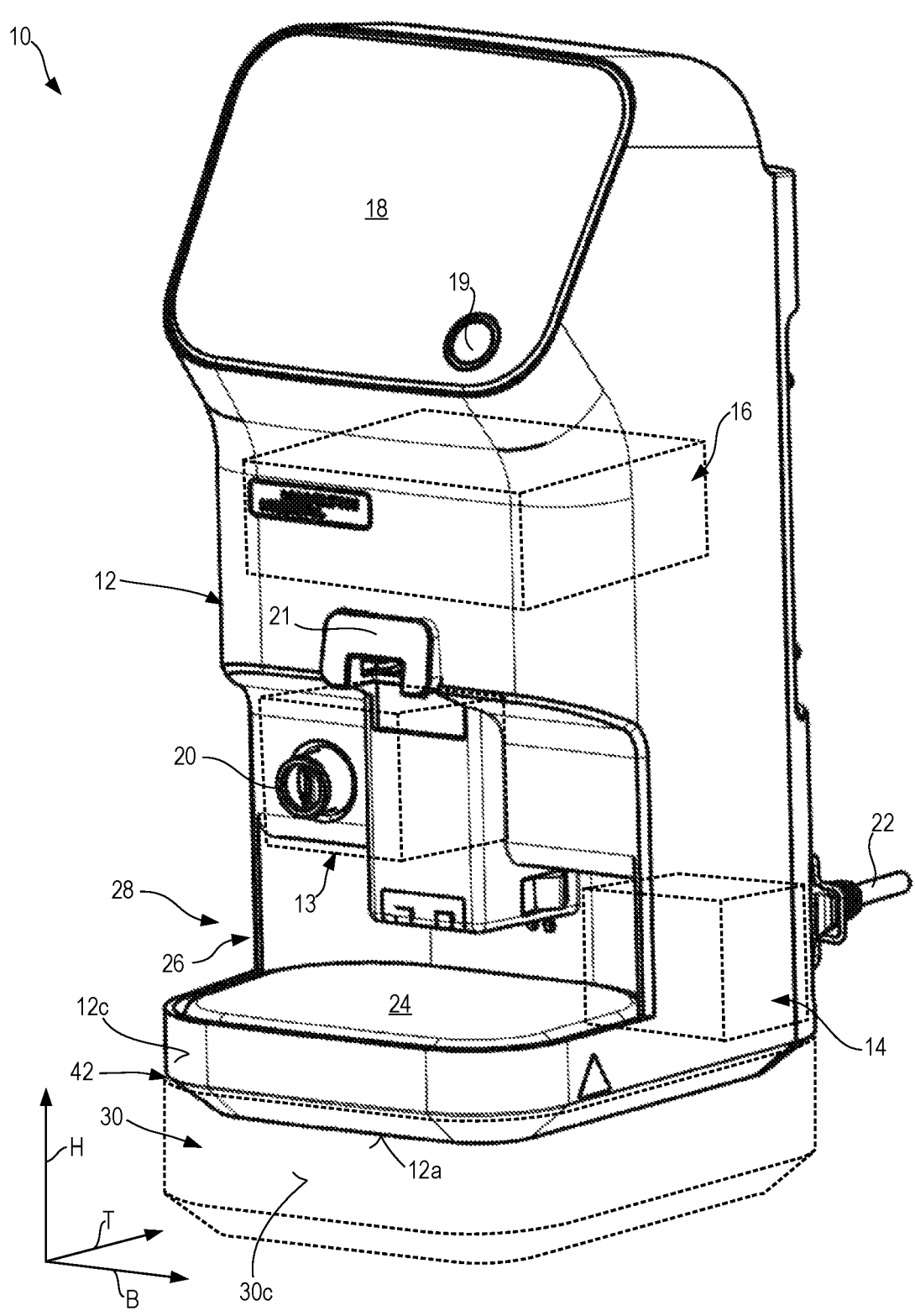
FIG. 1 A perspective view obliquely from the front and above of a portable respiratory device according to the invention, FIG. 2 A rear view of the respiratory device of FIG. 1, FIG. 3 A perspective view obliquely from the front and above of a second power supply, as indicated in FIG. 1 by a dashed line, and FIG. 4 The portable respiratory device of FIG. 1 with container inserted in it with liquid reservoir and with a connected respiratory hose.
Figure 2:
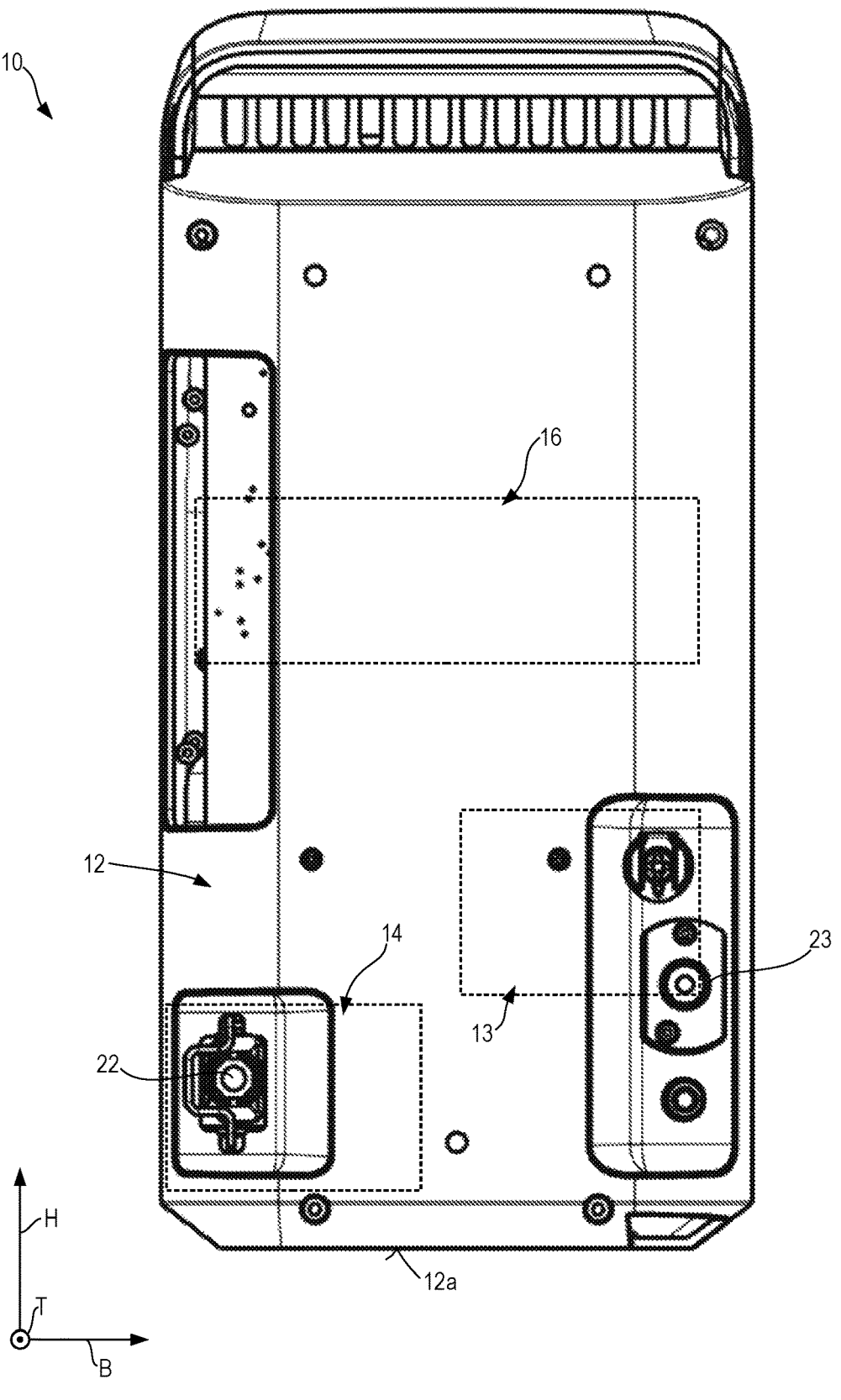

Referring now to the drawings wherein the showings are for the purpose of illustrating preferred and alternative embodiments of the invention only and not for the purpose of limiting the same, in FIGS. 1 and 2, an embodiment of a portable respiratory device according to the present invention is labelled generally by 10. The respiratory device 10 comprises a housing 12 in which a respiratory gas conveying device 13 in the form of a fan, a first power grid-based power supply 14, customarily also referred to as 'power unit', a control device 16, and an input/output device 18 are accommodated. Devices inside the housing 12 are depicted merely by dotted lines.

The respiratory gas conveying device 13 aspirates as a fan ambient air through an aspirating port (not depicted) and delivers it at a respiratory gas housing outlet 20 to a respiratory gas line connected to the respiratory gas housing outlet 20 but not depicted here. The respiratory gas conveying device 13 produces sufficient excess pressure in order to convey the aspirated ambient air not only up to the respiratory gas housing outlet 20 but through the respiratory gas line connected to the latter up to the patient.

In the example depicted here, the respiratory gas housing outlet 20 opens into a liquid reservoir container not depicted in the drawings of a humidification device explained further below.

A connection of a respiratory gas hose—preferably heatable to prevent condensation—leading to the patient can take place at the connecting formation 21, from where inspiratory respiratory gas after passing through the liquid reservoir container of the humidification device is supplied to the patient.

The respiratory device 10 of the embodiment example is a high-flow respiratory device 10, which independently of the respiratory rhythm of the ventilated patient continuously supplies inspiratory respiratory gas to the ventilated patient, including during the latter's expiratory phase. The invention is not, however, limited to this type of device.

The control device 16 is connected with the respiratory gas conveying device 13, the first power supply 14, and the input/output device 18 for signal transmission, such that the control device 16 receives for further processing control commands and/or parameters input into the input/output device 18 can transmit control commands to the respiratory gas conveying device 13, to the first power supply 14, and to the input/output device 18. Besides the possibility of transmitting control commands, the control device 16 can, via the signal-transmitting connection, gather operational parameters of the respiratory gas conveying device 13, the first power supply 14, and the input/output device 18 and thus monitor their operation. Likewise the control device 16 can transmit data to the input/output device 18, in order to display them discernibly to the outside and/or output them at the input/output device 18.

The first power supply 14 is connectable through a power cable 22 with a power grid voltage source (not shown), for instance an electric socket, for connecting to a public power grid.

23 denotes a connecting formation for connecting a further respiratory gas source with a further respiratory gas preferably different from the ambient air. Thus the ambient air aspirated by the respiratory gas conveying device 13 can be mixed with a further gas in the respiratory device 10 before dispensing to the respiratory gas housing outlet 20.

The input/output device 18 is preferably inclined about a pitch axis parallel to the width direction B, such that its input surface 18*a* is easily reached by operating personnel. The input surface 18*a* can for example be a touch-sensitive screen, also referred to as a touch screen. Alternatively or additionally to merely demarcated buttons with functional allocation, as are typical for touch-sensitive sensitive screens, the input/output device 18 can also comprise one or several switches, such as pushbutton switches, rotary switches, and the like. For example, the on/off switch 19 may be mentioned which is configured as a mechanical pushbutton switch.

The respiratory device 10 is depicted in FIGS. 1 and 2 oriented ready for a respiratory operation.

As a further functional facility, the respiratory device 10 exhibits a hot plate 24 of a humidification device 26, the liquid reservoir of which (not shown) can be inserted in the recess 28 at the front side of the housing 12. The hot plate 24 of the humidification device 26 is also controlled by the control device 16. To this end, the control device 16 can be connected for signal transmission with one or several humidity sensors, which detect a humidity of the inspiratory respiratory gas conveyed by the respiratory gas conveying device 13 after passing through the humidification device 26 and where applicable also before passing through the latter and transmit it to the control device 16.

Since the humidification device 26 with the liquid reservoir exhibits a comparatively high weight per unit volume, the humidification device 26 is arranged in the vertical direction H as far down as possible in the housing 12 in order to achieve the lowest possible center of gravity of the respiratory device 10. For this reason, the first power supply 14 which likewise exhibits high weight per unit volume is also arranged as far down as possible in the housing 12. The liquid reservoir of the humidification device 26 and the first power supply are preferably situated in the bottom third of the housing 12.

Figure 3:
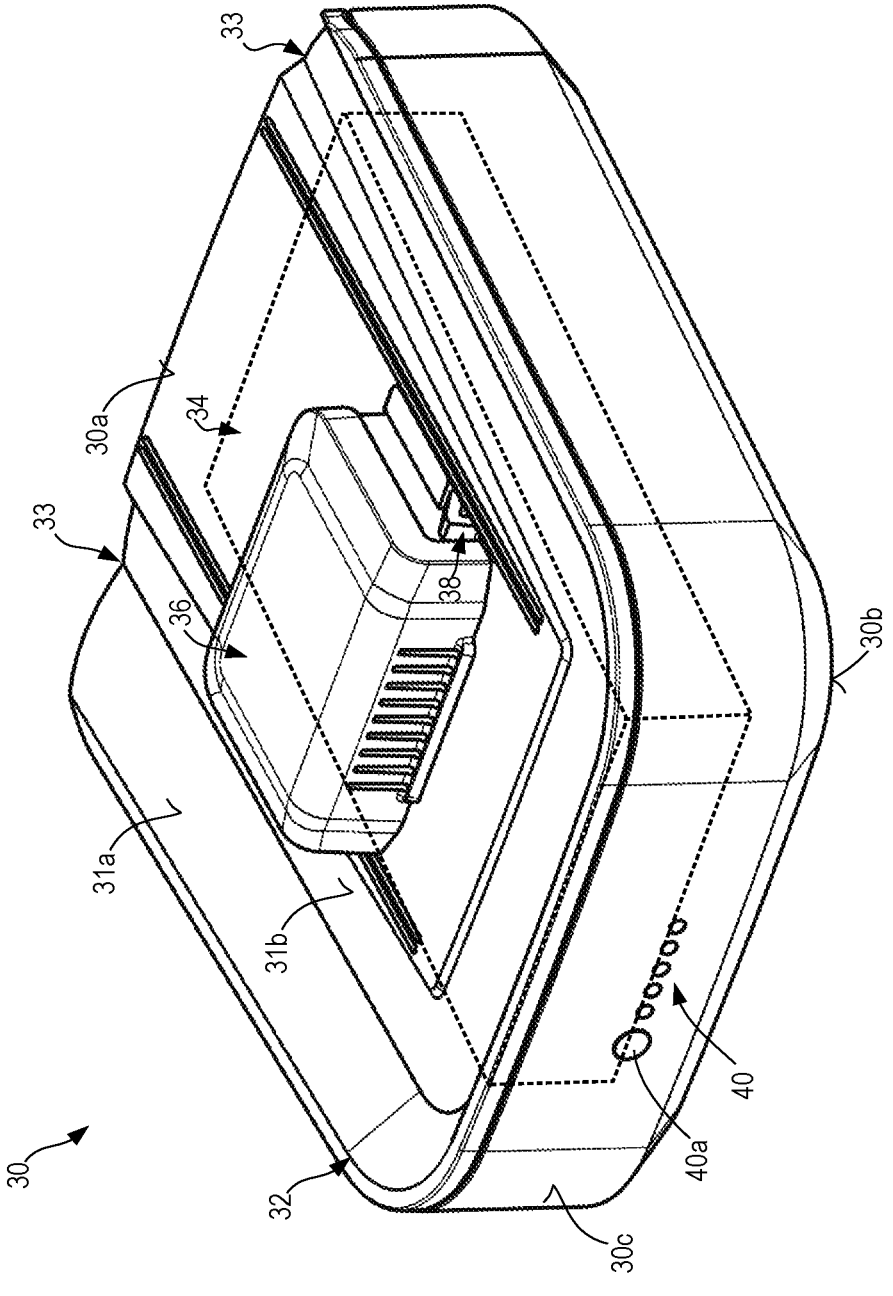
Figure 3:
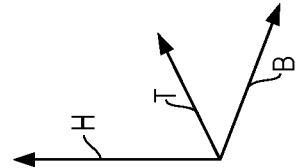

The respiratory device 10 furthermore exhibits a second power supply 30 shown in in FIG. 3, which in the depicted preferable embodiment exhibits a power supply housing 32 configured separately from the housing 12 of the respiratory device 10. The second power supply 30 is not a power grid-based power supply like the first power supply 14, instead exhibiting an electrical energy storage device 34 which is also referred to hereunder as an "electricity storage device".

The electricity storage device 34 is preferably a multiply rechargeable battery, for example a lithium-ion battery. The electricity storage device can, however, also exhibit a different type of batteries and/or at least one capacitor as electrical energy storage device.

Since the respiratory device 10 can be operated with and without the second power supply 30, the second power supply 30 is indicated in FIG. 1 only by a dashed line.

The second power supply 30 can be physically coupled in a detachable manner to the underside 12a of the housing 12 of the respiratory device 10 in such a way that in the coupled state the second power supply 30 is moveable together with the housing 12. In the uncoupled state, the housing 12 can rest on its underside 12a.

The second power supply 30 exhibits at its upper side 30a a coupling formation 36 which can be brought into current-transmitting mechanically positive-locking engagement with a mating coupling formation at the underside 12a of the housing 12. As FIG. 3 shows, the coupling formation 36 is configured as a projection. The mating coupling formation (not shown) at the underside 12a of the housing 12 is therefore configured in the form of a recess. A locking device 38 locks the second power supply 30 in a ready state for a transmission of electrical energy from the second power supply 30 to the rest of the respiratory device 10. The locking device 38 can be pre-tensioned to latch automatically and can for example be unlockable through an actuation intervention on the underside 30b of the second power supply 30 for uncoupling the second power supply 30 from the housing 12 of the respiratory device 10.

At its front side there can be arranged in the power supply housing 32 a charging state display 40, which for example can comprise a plurality of LEDs of which a greater number is illuminated, the more strongly the electricity storage device 34 is charged. Additionally or alternatively, the charging state display 40 can change its illumination color, for instance from green to red and vice versa, in order to communicate additional information such as for example the imminent occurrence of an operation end of the second power supply 30 due to emptying of the electricity storage device 34. The charging state display 40 can be activated by means of a pushbutton switch 40a, which for the purpose of energy savings displays the charging state of the electricity storage device 34 only on actuation of the pushbutton switch 40a and only for a predetermined short time of a few seconds.

When the second power supply 30 is arranged operationally at the housing 12, the control device 16 can also control the operation of the second power supply 30. For example, through operator input it can be defined whether when both power supplies 14 and 30 are available as current supplier, the respiratory device should be supplied with electrical energy through the first power supply 14 or through the second power supply 30. If the first power supply 14 is unavailable, for instance because of a power failure or because the first power supply 14 is faulty or because the power cable 22 is missing, the respiratory device 10 is automatically supplied with electrical energy by the second power supply 30.

When the first power supply 14 is available as current supplier, the control device 16 can initiate a charging of the electricity storage device 34 by the first power supply 14 provided that after supplying the operationally important functional devices such as the respiratory gas conveying device 13, and the control device 16 itself, where applicable also the input/output device 18 and/or the humidification device 26, there are available sufficient reserves for charging the electricity storage device 34.

The second power supply 30 acts at the respiratory device 10 like an interruption-free power supply, i.e. a failure of the power supply of the respiratory device 10 through the first power supply 14 is compensated for by the second power supply 30 in such a short time that no appreciable interruption of the respiratory operation of the respiratory device 10 occurs. In practice, this means that within no later than 50 ms after a failure of the first power supply 14, the second power supply 30 provides electrical energy to the functional devices thus far supplied by the first power supply 14.

The second power supply 30 is attachable to the underside 12a of the housing 12 since the second power supply 30 exhibits an above-average high weight relative to its volume and consequently can contribute to a desirably low center of gravity of the entire respiratory device 10 including the second power supply 30.

As FIG. 1 indicates, a lateral surface 30c encircling a vertical axis which is parallel to the vertical direction H joins in an essentially flush manner just such a lateral surface 12c of the housing 12 at its lower end region, for instance between the hot plate 24 and the underside 12a of the housing 12.

The housing 12 is a tower housing, i.e. it has in the vertical direction H a significantly greater dimension than in the width direction B and in the depth direction T. In the depicted example, the dimension in the width direction in the region of the housing 12 which exhibits the lateral surface 12c is approximately the same size as the dimension in the depth direction. Between the lateral surface 12c and contact surface of the housing 12 there can be configured a chamfer, which as a complementary configuration of a chamfer 31*a* can preferably also be configured at the upper side 30*a* of the second power supply 30 and/or of the power supply housing 32 respectively. Thus the second power supply 30 can be detachably coupled with the underside 12*a* of the housing 12 with very little free play, in a highly stable manner and with great strength.

The chamfer 31*a* serves besides as the aforementioned first surface section of the upper side 30*a* for the drainage of liquid from the outer wall of the respiratory device to a predetermined drainage location 33. In the present case there exist two drainage sites 33.

The chamfer 31*a* is inclined in the direction towards the body center of the second power supply 30. The chamfer 31*a* is in addition curved several times about an axis of curvature parallel to the vertical direction, such that the chamfer 31*a* can extend both over the front side which is opposite to the rear side shown in FIG. 2 and over the two sides of the respiratory device 10 adjoining the front side.

At the geodetically lower-lying edge of the chamfer 31*a* there adjoins a second surface region 31*b*, which is inclined in such a way that the drainage sites 33 are the geodetically lowest locations of the surface region 31*b*, such that liquid overflowing from the chamfer 31*a* onto the second surface region 31*b* flows onward gravitationally-driven to the drainage sites 33.

The chamfer 31*a* begins immediately at the outer edge of the upper side 30*a* of the power supply housing 32, such that liquid which gravitationally-driven runs down the lateral surface 12*c* of the housing 12 to the joint line 42 between the housing 12 and the power supply housing 32, on reaching the joint line is conducted first by the chamfer 31*a* and subsequently by the second surface region 31*b* from the joint line 42 to the drainage sites 33.

In the depicted embodiment example, the vertical direction H proceeds in parallel to the gravitational direction, but in the opposite direction. As can be discerned in particular in FIG. 1, the second power supply 30 coupled with the housing 12 lies completely within a footprint of the housing 12 projected along the gravitational direction and does not project sideways beyond it. The second power supply 30 also does not retreat behind this projected footprint of the housing 12, but rather corresponds in its extension, in a plane spanned by the width direction B and the depth direction T, essentially to the footprint area of the housing 12.

Figure 4:
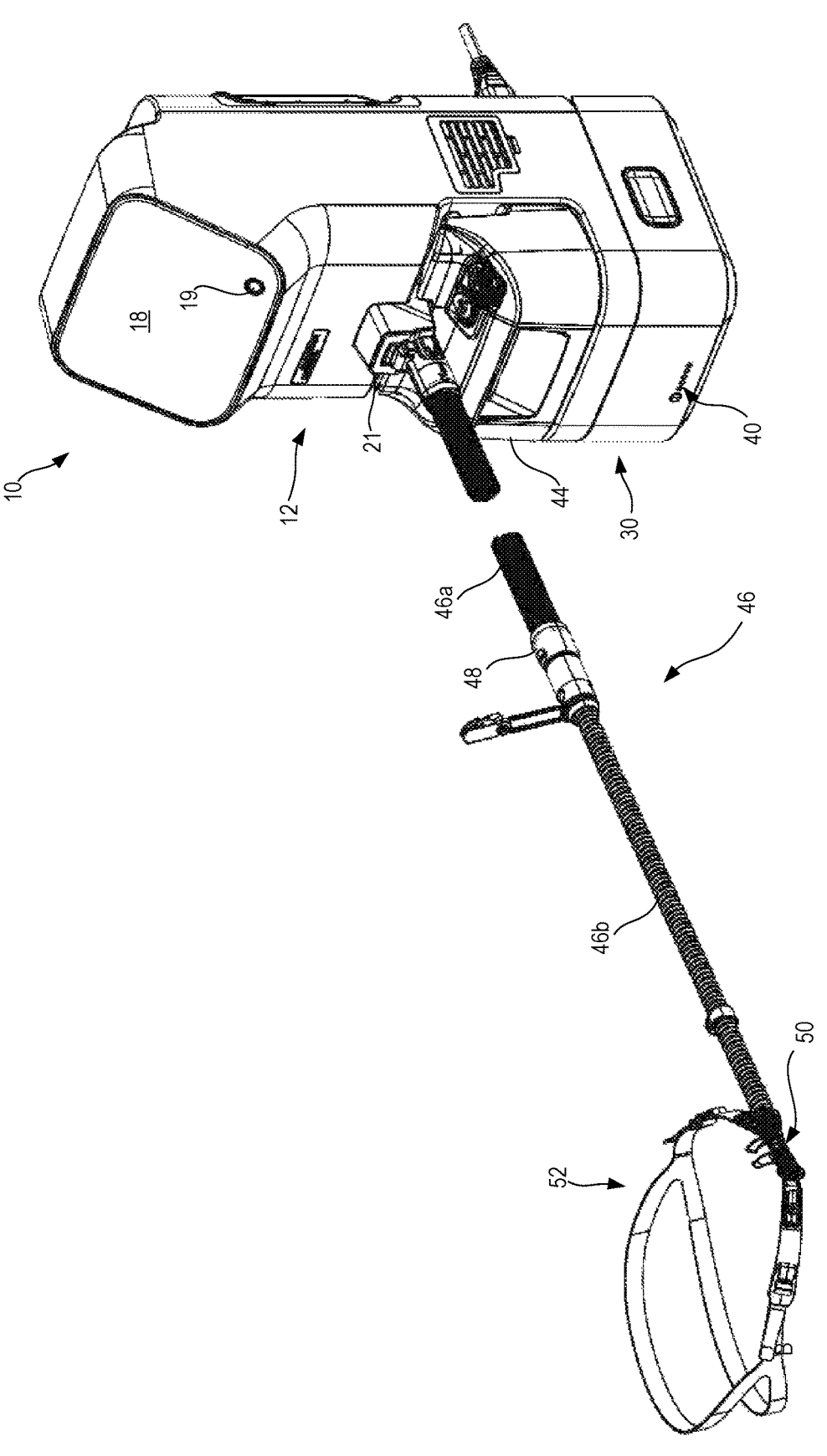

In FIG. 4, the respiratory device 10 of FIG. 1 is depicted with a liquid reservoir container 44 which is inserted in the recess 28. With the connecting formation 21 there is coupled a respiratory hose 46, which through the humidification device 26 conducts conditioned respiratory gas to a patient (not shown).

At the end of a first section 46*a* of the respiratory hose 46 remote from the respiratory device 10, there is arranged a temperature sensor 48 which detects the temperature of the respiratory gas in the respiratory hose 46, in particular at the end of the first section 46*a*, and transmits it to the control device 16 either via radio or through a cable led in or at the respiratory hose 46, which during the coupling of the respiratory hose 46 with the connecting formation 21 is preferably automatically connected for signal transmission with the control device 16.

Starting from the temperature signal of the temperature sensor 48, the control device 16 can, in particular when the respiratory device 10 is supplied with electrical energy only by the second power supply 30, control the operation of the hot plate 24, but also that of a heating device which may possibly be provided in the respiratory hose 46, in such a way that the respiratory gas at the temperature sensor 48 exhibits a temperature within a predetermined temperature range, for instance within a temperature range from 30° C. to 40° C., preferably from 33° C. to 38° C., especially preferably from 35° C.

The first section 46*a* of the respiratory hose 46 situated nearer the respiratory device 10 is depicted shortened in FIG. 4.

To the first section 46*a* there is attached a second section 46*b* of the respiratory hose 46, at the end of which there is arranged a nasal cannula 50 which via a headband 52 can be fixed to the head of the patient in a manner which is known per se. The respiratory gas can be administered continuously to the patient via the nasal cannula 50.

While considerable emphasis has been placed on the preferred embodiments of the invention illustrated and described herein, it will be appreciated that other embodiments, and equivalences thereof, can be made and that many changes can be made in the preferred embodiments without departing from the principles of the invention. Furthermore, the embodiments described above can be combined to form yet other embodiments of the invention of this application. Accordingly, it is to be distinctly understood that the foregoing descriptive matter is to be interpreted merely as illustrative of the invention and not as a limitation.

The invention claimed is:

1. A portable respiratory device for supplying respiratory gas to a living organism, comprising:
   a housing,
   a respiratory gas conveying device which is configured to convey inspiratory respiratory gas to a respiratory gas housing outlet of the housing,
   an input/output device for the input of control commands and for the output of information,
   a control device which is connected for signal transmission with the input/output device and with the respiratory gas conveying device,
   a first, power grid-based power supply which is configured for current-transmitting connection with a power grid voltage source external to the respiratory device and which is configured and arranged for supplying the control device, the input/output device, and the respiratory gas conveying device with current,
   a second, storage-based power supply which exhibits an electricity storage device for storing electrical energy and which is configured at least for supplying the respiratory gas conveying device with current,
   a humidification device which is configured to humidify the inspiratory respiratory gas, where the humidification device can be supplied with current both by the first and by the second power supply,
   wherein the respiratory gas conveying device, the input/output device, and the control device are accommodated in the housing,
   wherein the second power supply is part of a power supply housing that is separate from the housing of the respiratory device and is physically couplable in a detachable manner with the housing of the respiratory device for common movement,
   wherein when looking at the operationally ready respiratory device, the second power supply is arranged under the humidification device,
   wherein the first power supply is accommodated in the housing of the respiratory device, where the respiratory device can be supplied with electrical energy solely by the first power supply when the second power supply is separated from the housing of the respiratory device, wherein the housing of the respiratory device is configured to direct a liquid on or within the housing downwardly by action of gravity towards the power supply housing, wherein the power supply housing includes an upwardly facing drainage arrangement positioned to receive the liquid from on or within the housing, the drainage arrangement including at least one drainage surface which in a targeted manner directs the liquid impinging thereon from the housing away from the second power supply and to at least one defined drainage location in the power supply housing.

2. The respiratory device according to claim 1, wherein the second power supply is also configured for supplying the control device and the input/output device with current.

3. The respiratory device according to claim 1, wherein the electricity storage device of the second power supply is chargeable by the first power supply.

4. The respiratory device according to claim 1, wherein the electricity storage device of the second power supply is chargeable by the first power supply, where the control device is configured to control a charging process of the electricity storage device by the first power supply.

5. The respiratory device according to claim 1, wherein the second power supply is configured as an interruption-free power supply for the case of an end of a power supply to the respiratory device by the first power supply.

6. The respiratory device according to claim 1, wherein during operational positioning of the respiratory device, the second power supply is arranged in the lowest 20% of the overall height extension of the respiratory device.

7. The respiratory device according to claim 1, wherein during operational positioning of the respiratory device, the second power supply is arranged in the lowest 20% of the overall height extension of the respiratory device with the second power supply being the lowest functional device of the respiratory device when it includes the second power supply.

8. The respiratory device according to claim 1, wherein the power supply housing, when looking at an operational positioning of the respiratory device, is completely accommodated inside a footprint of the housing of the respiratory device projected in the gravitational direction.

9. The respiratory device according to claim 1, wherein the housing is a tower housing whose largest dimension during operational positioning is the vertical dimension.

10. The respiratory device according to claim 1, wherein the respiratory device comprises a heatable respiratory gas line which leads from the respiratory device to the patient.

11. The respiratory device according to claim 10, wherein the control device is configured, when the charging state of the electricity storage device drops below a first charging state limit, to shut down an evaporation device of the humidification device, and when the charging state drops below a second charging state limit which is quantitatively lower than the first charging state limit, to shut down a heating device of the respiratory gas line.

* * * * *